(12) United States Patent
Smith

(10) Patent No.: US 9,883,898 B2
(45) Date of Patent: Feb. 6, 2018

(54) PEDICLE SCREW WITH ELECTRO-CONDUCTIVE COATING OR PORTION

(71) Applicant: Jeffrey Scott Smith, Granbury, TX (US)

(72) Inventor: Jeffrey Scott Smith, Granbury, TX (US)

( * ) Notice: Subject to any disclaimer, the term of this patent is extended or adjusted under 35 U.S.C. 154(b) by 356 days.

(21) Appl. No.: 14/821,541

(22) Filed: Aug. 7, 2015

(65) Prior Publication Data

US 2016/0038205 A1    Feb. 11, 2016

Related U.S. Application Data

(60) Provisional application No. 62/034,420, filed on Aug. 7, 2014.

(51) Int. Cl.
| | |
|---|---|
| *A61B 17/04* | (2006.01) |
| *A61B 17/86* | (2006.01) |
| *A61F 2/08* | (2006.01) |
| *A61B 17/70* | (2006.01) |
| *A61N 1/05* | (2006.01) |
| *A61B 17/16* | (2006.01) |
| *A61N 1/36* | (2006.01) |

(52) U.S. Cl.
CPC ........ *A61B 17/866* (2013.01); *A61B 17/1655* (2013.01); *A61B 17/7092* (2013.01); *A61N 1/0558* (2013.01); *A61B 17/8615* (2013.01); *A61B 17/8635* (2013.01); *A61N 1/3606* (2013.01)

(58) Field of Classification Search
None
See application file for complete search history.

(56) References Cited

U.S. PATENT DOCUMENTS

| | | | |
|---|---|---|---|
| 3,499,222 A | 3/1970 | Edelman | |
| 4,537,185 A | 8/1985 | Stednitz | |
| (Continued) | | | |

FOREIGN PATENT DOCUMENTS

EP         1912575         1/2011

OTHER PUBLICATIONS

U.S. Appl. No. 12/132,476, Jan. 18, 2011, Office Action.
(Continued)

*Primary Examiner* — Sameh Boles
(74) *Attorney, Agent, or Firm* — Workman Nydegger

(57) ABSTRACT

A pedicle screw may include an electrically conductive portion formed from a material having a greater electrical conductivity than that of the base material from which the screw is formed. The electrically conductive portion preferentially channels electrical energy supplied by an electrical probe to a location of the electrically conductive portion facing the nerve root. The portion thus provides a sort of electrical highway that helps to focus the electrical energy applied to the pedicle screw in a particular direction, towards the presumed location of the nerve root. As an alternative to placement of the electrically conductive portion in the pedicle screw itself, the electrically conductive portion could be placed within a tap that is used in preparing the pedicle for receipt of the pedicle screw (e.g., in forming the threaded structure in the pedicle bone into which the pedicle screw will then be placed).

15 Claims, 7 Drawing Sheets

(56) References Cited

U.S. PATENT DOCUMENTS

| | | | |
|---|---|---|---|
| 4,858,601 | A | 8/1989 | Glisson |
| 5,019,079 | A | 5/1991 | Ross |
| 5,324,199 | A | 6/1994 | Branemark |
| 5,769,852 | A | 6/1998 | Branemark |
| 5,989,025 | A | 11/1999 | Conly |
| 6,015,937 | A | 1/2000 | Branemark |
| 6,033,438 | A | 3/2000 | Bianchi |
| 6,053,916 | A | 4/2000 | Moore |
| 6,174,330 | B1 | 1/2001 | Stinson |
| 6,224,598 | B1 | 5/2001 | Jackson |
| 6,248,105 | B1 | 6/2001 | Schlapfer |
| 6,280,442 | B1 | 8/2001 | Barker |
| 6,302,888 | B1 | 10/2001 | Mellinger |
| 6,440,137 | B1 | 8/2002 | Horvath |
| 6,443,953 | B1 | 9/2002 | Perra |
| 6,565,567 | B1 | 5/2003 | Haider |
| 6,755,829 | B1 | 6/2004 | Bono |
| 6,921,403 | B2 | 7/2005 | Cragg |
| 7,186,255 | B2 | 3/2007 | Baynam |
| 7,235,076 | B2 | 6/2007 | Pacheco |
| 7,261,716 | B2 | 8/2007 | Strobel |
| 7,294,128 | B2 | 11/2007 | Alleyne |
| 7,691,129 | B2 | 4/2010 | Felix |
| 7,699,849 | B2 | 4/2010 | Eckman |
| 7,871,413 | B2 | 1/2011 | Park |
| 7,967,850 | B2 | 6/2011 | Jackson |
| 8,016,862 | B2 | 9/2011 | Feliz |
| 8,016,866 | B2 | 9/2011 | Warnick |
| 8,197,517 | B1 | 6/2012 | Lab |
| 8,206,391 | B2 | 6/2012 | Betts |
| RE44,268 | E | 6/2013 | Kambin |
| 8,740,956 | B2 | 6/2014 | Smith |
| 8,784,411 | B2 | 7/2014 | Leuthardt |
| 8,808,320 | B2 | 8/2014 | Batten |
| 8,845,693 | B2 | 9/2014 | Smith |
| 8,986,318 | B2 | 3/2015 | Smith |
| 9,084,633 | B2 | 7/2015 | Smith |
| 2002/0038123 | A1 | 3/2002 | Visotsky |
| 2004/0220567 | A1 | 11/2004 | Eisermann |
| 2004/0220575 | A1 | 11/2004 | Biedermann |
| 2004/0243207 | A1 | 12/2004 | Olson |
| 2005/0203523 | A1 | 9/2005 | Wenstrom |
| 2005/0261695 | A1 | 11/2005 | Cragg |
| 2005/0277918 | A1 | 12/2005 | Shah |
| 2006/0089644 | A1 | 4/2006 | Felix |
| 2006/0271196 | A1 | 11/2006 | Saal |
| 2006/0276788 | A1 | 12/2006 | Berry |
| 2007/0055232 | A1 | 3/2007 | Colquhoun |
| 2007/0288004 | A1 | 12/2007 | Alvarez |
| 2008/0086129 | A1 | 4/2008 | Lindemann |
| 2008/0114364 | A1 | 5/2008 | Goldin |
| 2008/0287959 | A1 | 11/2008 | Quest |
| 2008/0306554 | A1 | 12/2008 | McKinley |
| 2009/0036934 | A1 | 2/2009 | Biedermann |
| 2009/0119280 | A1 | 5/2009 | Waters et al. |
| 2010/0063550 | A1 | 3/2010 | Felix |
| 2011/0125265 | A1 | 5/2011 | Bagga |
| 2011/0184447 | A1 | 7/2011 | Leibowitz |
| 2011/0264151 | A1* | 10/2011 | Davis ................ A61B 17/7035 606/305 |
| 2012/0179183 | A1 | 7/2012 | Stad |
| 2013/0338492 | A1 | 12/2013 | Munro |
| 2014/0114341 | A1 | 4/2014 | Wolff |
| 2014/0148853 | A1 | 5/2014 | Smith |
| 2014/0171955 | A1 | 6/2014 | Smith |
| 2014/0214099 | A1 | 7/2014 | Smith |
| 2014/0276840 | A1 | 9/2014 | Richter |
| 2015/0173844 | A1 | 6/2015 | Smith |

OTHER PUBLICATIONS

U.S. Appl. No. 12/132,476, Jun. 22, 2011, Final Office Action.
U.S. Appl. No. 13/401,339, Aug. 9, 2013, Office Action.
U.S. Appl. No. 12/132,476, Sep. 24, 2013, Office Action.
U.S. Appl. No. 13/401,339, Dec. 20, 2013, Final Office Action.
U.S. Appl. No. 12/132,476, Jan. 24, 2014, Notice of Allowance.
U.S. Appl. No. 13/401,339, Apr. 23, 2014, Advisory Action.
U.S. Appl. No. 13/401,339, May 16, 2014, Notice of Allowance.
U.S. Appl. No. 13/427,865, May 30, 2014, Restriction Requirement.
U.S. Appl. No. 13/427,841, Jun. 17, 2014, Office Action.
U.S. Appl. No. 14/256,742, Sep. 23, 2014, Office Action.
U.S. Appl. No. 13/427,841, Sep. 25, 2014, Final Office Action.
U.S. Appl. No. 13/427,865, Nov. 3, 2014, Notice of Allowance.
U.S. Appl. No. 13/427,841, Mar. 4, 2015, Office Action.
U.S. Appl. No. 13/427,841, Oct. 5, 2015, Final Office Action.
U.S. Appl. No. 13/427,841, May 9, 2016, Office Action.
U.S. Appl. No. 13/427,841, Feb. 7, 2017, Notice of Allowance.
Young, Robin "The Ten Best New Spine Technologies for 2013" published Nov. 10, 2013, accessed on May 25, 2016 at https://ryortho.com/2013/11/the-ten-best-new-spine-technologies-for-2013/ 8 pages.

* cited by examiner

PEDICLE SCREW WITH ELECTRO-CONDUCTIVE COATING OR PORTION

CROSS-REFERENCE TO RELATED APPLICATIONS

The present application claims the benefit under 35 USC § 119(e) of U.S. patent application Ser. No. 62/034,420, filed Aug. 7, 2014 and entitled "APPLICATION OF AN ELECTRICALLY CONDUCTIVE COATING TO A PEDICLE SCREW", the disclosure of which is incorporated by reference in its entirety.

BACKGROUND OF THE INVENTION

1. The Field of the Invention

The present invention generally relates to medical devices and methods of use, particularly to pedicle screw systems and methods for their installation.

2. The Relevant Technology

Over the past several decades, spinal surgery has increasingly become an important option available to surgeons and patients in treating issues related to the spine. Because the spine generally provides support and movement for the body, a problem with the spine (e.g., a back disorder) can disrupt even the simplest life activities. In general, thousands of surgical fusions of the spine are performed each year in an attempt to decrease pain and to increase function for the patient. Stabilization of the spine through fusion may be accomplished in a variety of ways, including, for example, the use of pedicle screws, e.g., often used to assist in the fixation of the lumbar and thoracic portions of the spine. Such pedicle screws are generally biocompatible screws that are typically anchored into a vertebra at the pedicle, which is a projection from the body of a given vertebra that connects the body of the vertebra to an arch of the vertebra. Vertebrae generally have two pedicles.

Placement of pedicle screws allows the surgeon to minimize or limit the motion of the spine during the healing process, so as to achieve the desired fixation. Placement of pedicle screws is generally considered a relatively safe procedure, although the procedure is not without some inherent risks. For example, such risks include, but are not limited to, screw fracture and/or loosening, increased incidence of infection, and nerve irritation or injury from unintentional interaction between the pedicle screw and the intimately associated nerve root. For example, each pedicle is closely related to its associated nerve root which passes medial and inferior to the pedicle before it exits the spinal canal through the neuroforamin. Due to the proximity of the nerve root to the pedicle, the nerve is at risk for irritation or injury in the event that the pedicle screw breaches the medial or inferior wall of the pedicle.

Numerous studies have demonstrated this risk, with the incidence reported from anywhere between 2 and 20 percent. Encroachments of not more than within 2 millimeters are less likely to be problematic. In an attempt to identify pedicle screws which have breached the wall of the pedicle, and are therefore more likely to cause nerve root irritation, neuromonitoring equipment has been employed. For example, after insertion of the pedicle screw, the screw may be stimulated with an electrical probe. Electrical current enters through the screw head, which is touched by the stimulating probe, and then disperses into the patient through the pedicle screw. Pedicle screws are generally manufactured from metal, with titanium being the most common. Discharge of electrical energy is intended to follow the path of least resistance, e.g., discharging preferentially through the portion of the pedicle screw which has breached the wall of the pedicle.

While such methods can be helpful in determining whether particular placement of the pedicle screw is more likely to result in nerve pain, there exists a continuing need for improved pedicle screws and methods to address these issues.

BRIEF SUMMARY

The present invention involves the application of a coating, or otherwise providing a portion to a pedicle screw which will preferentially channel the electrical energy supplied by an electrical probe to the pedicle screw head during neuromonitoring. For example, one problem with existing systems and methods is that titanium is a relatively poor conductor of electricity compared to other metals, such as gold or silver. In addition, the pedicle screw is typically homogenous, e.g., pure, titanium, so that the electrical current is typically free to pass through the pedicle screw in any manner and direction. In practice, the hope during neuromonitoring is that the path of least electrical resistance will be towards any breach adjacent the nerve root. Such is not always the case.

By providing an electrically conductive coating or portion which conducts electrical energy better than the other portions of the pedicle screw, the coating or portion provides a sort of electrical "highway" that will help to focus the electrical energy applied to the pedicle screw into a particular direction. The coating or portion can be specifically configured so that this directional "highway" is oriented towards the presumed location of the nerve root, which would increase the accuracy of information obtained during neuromonitoring.

While such features may be incorporated into a pedicle screw, it may also be possible to include similar features (e.g., an electrically conductive coating or portion) within a tap for insertion into a pedicle in preparation for placement of a pedicle screw. The electrical probe could be contacted with the electrically conductive portion of such a tap while the tap is positioned within the pedicle, so as to test the proposed pedicle screw placement corresponding to the placement of the tap. If the test shows no problems, then the pedicle screw may then be placed (such a screw need not include any electrically conductive portion, as the test has already been performed). If the test shows breach or otherwise too high a probability of nerve pain associated with pedicle screw placement in that position, then the tap may be repositioned, as needed.

According to an embodiment, a pedicle screw or a tap for insertion into a pedicle in preparation for placement of a pedicle screw is provided. Whether in the form of the pedicle screw itself, or a tap for insertion into the pedicle, in preparation for placement of a pedicle screw, the device may include a head and a shaft attached to the head, the shaft comprising a threaded portion, the shaft and head of the comprising a material having a first electrical conductivity. For example, in the case of a pedicle screw, the shaft and head may be formed of a biocompatible material (e.g., titanium). The device may further include an electrically conductive portion (e.g., a portion of the shaft). The electrically conductive portion of the shaft may be a different material that is coated on, or otherwise provided over the first material. The second material advantageously is selected to have greater electrical conductivity than the first material, to provide the desired directional "highway". The electrically conductive portion may extend longitudinally from the head of the device (screw or tap) to at least a distally disposed nerve root portion of the shaft. The electrically conductive portion may or may not terminate short of the distal end of the screw or tap device. The nerve root portion of the shaft may be oriented towards a nerve root associated with the pedicle into which the pedicle screw or tap is placed during use. In this way, the nerve root portion includes the electrically conductive portion, so that the "highway" leads from the head to the location on the screw or tap that is next to (e.g., facing and opposite) the nerve root when the screw or tap is inserted into the pedicle.

By way of example, the elongate electrically conductive portion may comprise a relatively narrow, elongate "strip" of the second material, e.g., disposed on or in one side of the shaft (e.g., on or in the side that is oriented towards the nerve root when the device is inserted into the pedicle). Such a strip of material may extend along the outside of the device, or a portion of it may be disposed internally. For example, in the case of a cannulated screw or tap, a portion of the electrically conductive portion could be placed inside the cannula of the device and then via a small passageway also coated with or otherwise provided with the second material, this upper portion of the electrically conductive portion could be connected to a patch of any desired shape or size on the outer surface of the screw (e.g., on the nerve root side, at the desired location between the distal and proximal ends). Such an embodiment may reduce or eliminate the loss of current as the electrical energy travels to the region of interest on the outside of the screw or tap device.

In embodiments where the coating or other electrically conductive portion is a narrow strip extending down one side of the device, a rotational marker on the device (e.g., on or in the head) could be used to confirm that the electrically conductive portion was appropriately directed towards the nerve root after insertion. The part of the strip that is in the head itself may serve as the marker, where there is a clear visual indicator that differentiates the strip or other portion from the surrounding material of the device. For example, the strip or other portion may simply be of a different color (e.g., gold verses grayish titanium). Other markers may also be employed.

The electrical energy applied to the pedicle screw (or tap) during the process of neurostimulation would be directed more effectively towards the nerve root instead of allowing the energy to be dissipated in a random manner throughout the entire screw. In another example, the electrically conductive portion could be placed circumferentially around the screw in the region near the nerve root. This may be roughly in the center of the screw, or perhaps a little more accurately in the second ⅓ of the screw length. The depth position within the pedicle would be similar where the device is a tap, although of course the proximal end of a tap device may be significantly lengthened. In any case, in such a manner, orientation of the electrically conductive portion would not be dependent on the rotation of the screw, although some electrical energy may also be lost to dissipation to the areas away from the nerve root, so that a directional embodiment may be preferred for better accuracy. Numerous other configurations will also be apparent to one of skill in the art.

Of course, another aspect of the present invention is directed to a method for neuromonitoring to verify correct placement of a pedicle screw into a pedicle. Such a method may include providing a pedicle crew or tap as described herein, inserting the screw or tap into the pedicle where the pedicle screw is to be placed, and applying an electrical current to the pedicle screw or tap (e.g., the head of either), so that the electrical current is directed from the head to the nerve root portion, along the electrically conductive portion of the device. Measured electrical current or other electrical characteristics associated with the neurostimulation may be compared to a threshold value, which comparison indicates to the surgeon whether such placement of a pedicle screw is appropriate, or too close to a nerve root associated with the pedicle, and likely to be a problem. If the neurostimulation checks out, then placement of the pedicle screw system may proceed. If the intended placement appears to present a risk of future nerve pain complaints, the screw or tap may be removed, and repositioned into a better position.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DETAILED DESCRIPTION OF THE PREFERRED EMBODIMENTS

I. Introduction

The proposed invention involves the application of a coating or otherwise providing a portion to a pedicle screw which preferentially channels electrical energy supplied by an electrical probe to the pedicle screw head during neuromonitoring. The coating or other portion provides a sort of electrical "highway" that helps to focus the electrical energy applied to the pedicle screw in a particular direction, towards the presumed location of the nerve root. As an alternative to placement of the electrically conductive portion in the pedicle screw itself, the coating or other portion could alternatively be placed within a tap that is used in preparing the pedicle for receipt of the pedicle screw (e.g., in forming the threaded structure in the pedicle bone into which the pedicle screw will then be placed). In such embodiments, the pedicle screw employed may then not necessarily include any such electrically conductive portion, as verifying the placement of the pedicle screw relative to its proximity to the nerve root may occur while the tap is inserted into the pedicle bone.

II. Exemplary Methods and Devices

Figure 1:
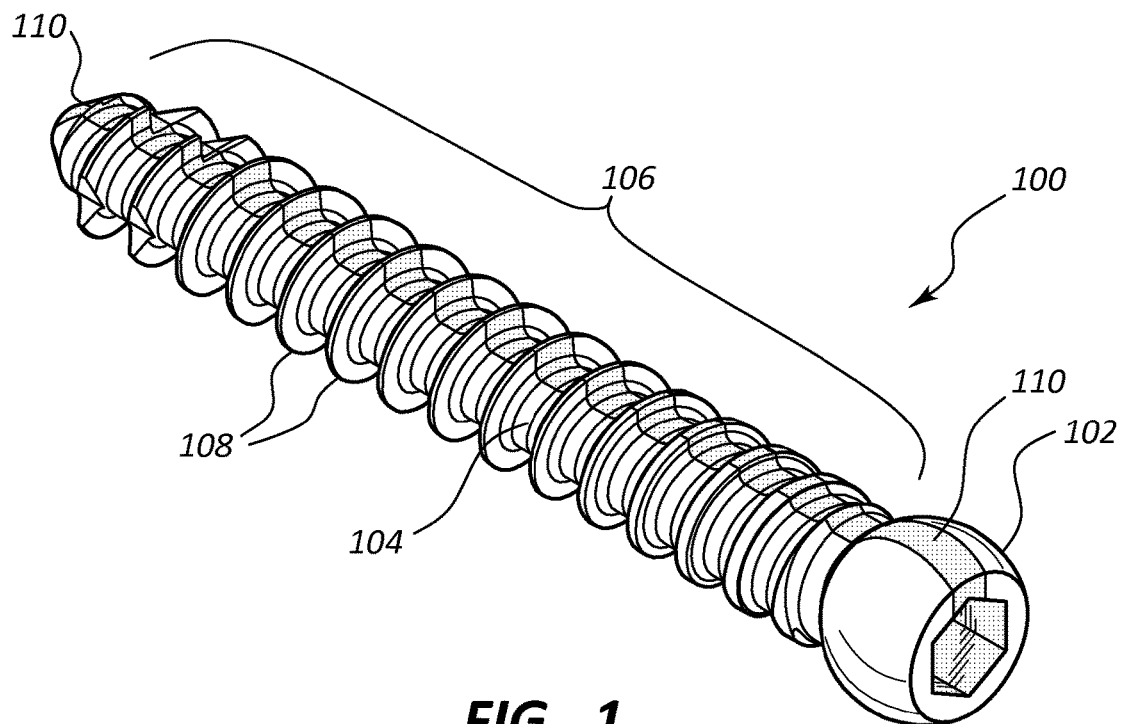
FIG. 1 is a perspective view of an exemplary pedicle screw including an portion disposed therein including enhanced electrical conductivity.

FIG. 1 illustrates an exemplary pedicle screw 100, which includes a head 102 (e.g., to be connected to a connecting rod of a pedicle screw system in the finished installed system) and a shaft 104. Shaft 104 may be integrally attached with head 102 (e.g., both formed from a single piece of metal or other suitable material). Shaft 104 is shown as including a threaded portion 106, including threads 108. The configuration of the shaft, threads, head, etc. of pedicle screw 100 may be according to any desired configuration, not necessarily limited to the configurations shown herein. By way of example, in an embodiment, only a portion of shaft 104 may be threaded, or substantially the entirety of shaft 104 may be threaded. In an embodiment, the shaft may include a portion or side thereof that is not threaded, e.g., as described in the inventor's earlier U.S. Pat. Nos. 8,740,956 and 9,084,633. Additional description of pedicle screws and associated systems and methods are described in the inventor's earlier U.S. Pat. Nos. 8,845,693; 8,986,318, and Publications 2015/0173844 and 20140148853. Each of the above patents and publications are herein incorporated by reference in its entirety.

As seen in FIG. 1, the pedicle screw 100 further includes an electrically conductive portion 110. Portion 110 may be a coating or layer, e.g., applied or otherwise provided on or in pedicle screw 100. In an embodiment, portion 110 comprises a material that is different from the material from which the remainder of the pedicle screw (e.g., the shaft and head, etc.) is formed. The material of portion 110 advantageously has an electrical conductivity that is greater than that of the base material from which the shaft and head is formed. For example, pedicle screws are typically formed of titanium, although titanium is not particularly electrically conductive. There are other materials that are much better electrical conductors than titanium (e.g., gold or silver). It may also be possible to form the head and/or shaft of the pedicle screw 100 from a material other than titanium, e.g., any desired biocompatible material may be employed. In an embodiment, the head 102 and/or shaft 104 may be formed from carbon (e.g., graphite). A metal or other electrically conductive portion (e.g., configured as an elongate strip) may be provided in or on the shaft (e.g., a metal strip press-fit into a graphite screw or tap), which directs conduction of the electrical current from the point where an electrical probe contacts the screw (e.g., head 102) down strip or other portion 110, to a location that is adjacent the nerve root. Such channeling of the electrical current improves the accuracy of readings taken during neuromonitoring, ensuring that the proposed placement of the pedicle screw will not result in unwanted interference with the nerve root, (e.g., causing nerve pain).

Where the pedicle screw includes an unthreaded portion in the nerve root portion thereof, e.g., as described in U.S. Pat. Nos. 8,740,956 and 9,084,633, the electrically conductive portion 110 may be aligned with the unthreaded portion, so that portion 110 runs down (e.g., down the center, or at least through) the unthreaded portion, as the purpose of each is to position the unthreaded portion so as to be opposite and facing the nerve root, which is the same desired positioning relative to electrically conductive portion 110. Such a configuration is shown in FIG. 5C.

In order to be effective, the coating or other portion 110 may have one or more of the following characteristics: (1) the coating or other portion provides preferential (i.e., increased) electrical conductivity as compared to the base metal or other base material; (2) the coating or other portion should be firmly adherent (i.e., it will not readily fall off or out) to the material of the pedicle screw; (3) the coating or other portion should be biocompatible at least in the context of a screw; and (4) the coating or other portion, and the base material should be compatible as far as galvanic corrosion is concerned, as least in the context of a screw.

Gold and silver have both been considered by the inventor for this purpose. After initial studies, the inventor believes that gold (e.g., gold plating) may be more appropriate. Gold as well as silver are easily bonded to most metals, including titanium. Gold and silver both have excellent electrical conductivity. Both gold and silver are over 1000 times more conductive than titanium. The electrical conductivity of silver and gold as compared to titanium is found below.

Silver $6.3 \times 10^7$ S/m
Gold $4.1 \times 10^7$ S/m
Titanium $1.78 \times 10^6$ S/m Silver unfortunately has biocompatibility concerns which may make its use in this application less desirable, although it may be perfectly suitable for incorporation into a tap for insertion into a pedicle in preparation for placement of a pedicle screw to follow, as the tap typically does not remain in place for relatively long. Gold has outstanding biocompatibility. It is quite possible that additional materials may be appropriate for the application. Silicon such as used in computer chips, may be an option for this purpose, or other synthetic materials which meet the previously mentioned criteria. Silicon or other synthetics may offer superior corrosion properties as compared to gold. While silicon appears to have only limited electrical conductivity in its pure form, it may be possible to dope silicon with one or more dopants to achieve higher electrical conductivity.

Table 1 shows electrical conductivities of various materials, which may be suitable for use in forming the portion 110, and/or the base material from which the shaft and head may be formed. Table 1 is non-exhaustive, and other materials may also be used. As described herein, the portion 110 may be formed from a material that has a greater electrical conductivity as compared to the surrounding material from which the remainder of the shaft and head may be formed, so as to create a sort of electrical "highway" along which the electrical current will preferentially be conducted (i.e., the path of least electrical resistance).

TABLE 1

| Material | Electrical Conductivity ($10^6$ Siemens/m) |
|---|---|
| Silver | 63 |
| Copper | 59 |
| Gold | 41 |
| Aluminum | 37 |
| Molybdenum | 19 |
| Zinc | 17 |
| Tungsten | 9 |
| Brass | 16 |
| Carbon | 6 |
| Nickel | 14 |
| Iron | 10 |
| Carbon Steels | ~6 |
| Palladium | 10 |
| Platinum | 9 |

TABLE 1-continued

| Material | Electrical Conductivity ($10^6$ Siemens/m) |
| --- | --- |
| Bronze | 7 |
| Titanium | 2 |
| Stainless Steels | 1-2 |

In an embodiment, the coating or other electrically conductive portion 110 may not extend around the full circumference of the pedicle screw, but may be positioned along one side thereof, In such embodiments, the width of the coating or portion 110 may be from 0.5 to 4 mm in width, from 1 to 3 mm in width, or from 1 to 2 mm in width. This may be relative to a typical pedicle screw, e.g., having a diameter of about 7.5 mm. For larger or smaller pedicle screws, the width may of course vary, in order to better accommodate placement and positioning of the width of the portion 110 opposite the nerve root during placement, so that the electrical current runs along a "directional highway" from the probe contact point (e.g., on the head 102) to the desired location opposite the nerve root, for improved accuracy.

Figure 2:
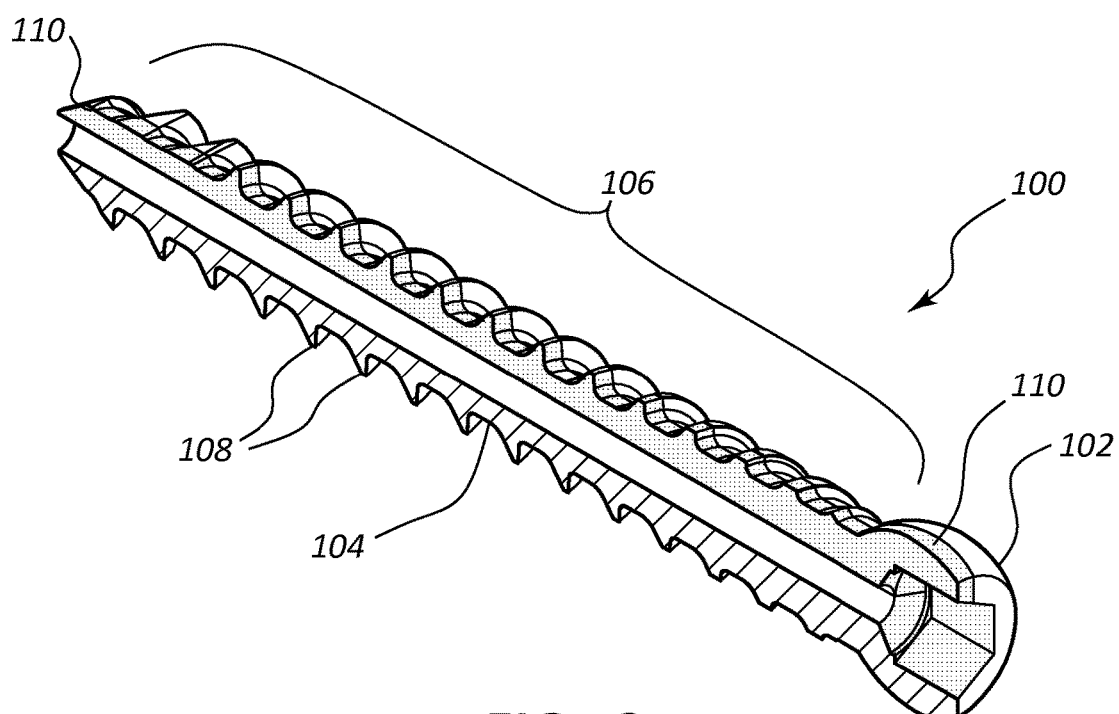
FIG. 2 is a cross-section of the pedicle screw of FIG. 1.

In the case of an applied coating, the coating to be approximately 5 to 50 microns, 5 to 20 microns, or about 10 microns thick. Actual selected thickness and width (e.g., linear width or arc length along a circumference) may be determined according to the particular materials selected. For example, a coating may be deposited by any suitable technique whether various deposition techniques as will be appreciated by those of skill in the art, or any other suitable process. In an embodiment, it may be preferable to machine or otherwise form a small groove through the threads or other portion of shaft 104 of the pedicle screw 100 to assist in application or placement of the coating or other portion 110. In an embodiment, an elongate rod or other configured portion 110 could be press fit or otherwise fixed within a groove formed into the base material of the screw. For example, the screw could be formed from graphite, titanium, or any other biocompatible material, and a rod or other portion 110 could be press fit into a groove machined or otherwise provided within the screw base material. As shown in FIG. 2, the portion 110 could extend through the full thickness of the screw or tap, e.g., to its center. In another embodiment, a groove could be provided, which does not extend through the full thickness.

In conclusion, the application of a material with superior electrical conductivity to the surface of a pedicle screw is proposed. The additional coating or portion 110 is designed to improve the ability of the surgeon to electrically test the pedicle screw for breach of the wall of the pedicle. Numerous materials are considered for this purpose such as gold plating, press-fitting of a metal rod (e.g., gold, stainless steel, cobalt-chromium alloy, etc.) into the screw base material, etc.

Figure 3:
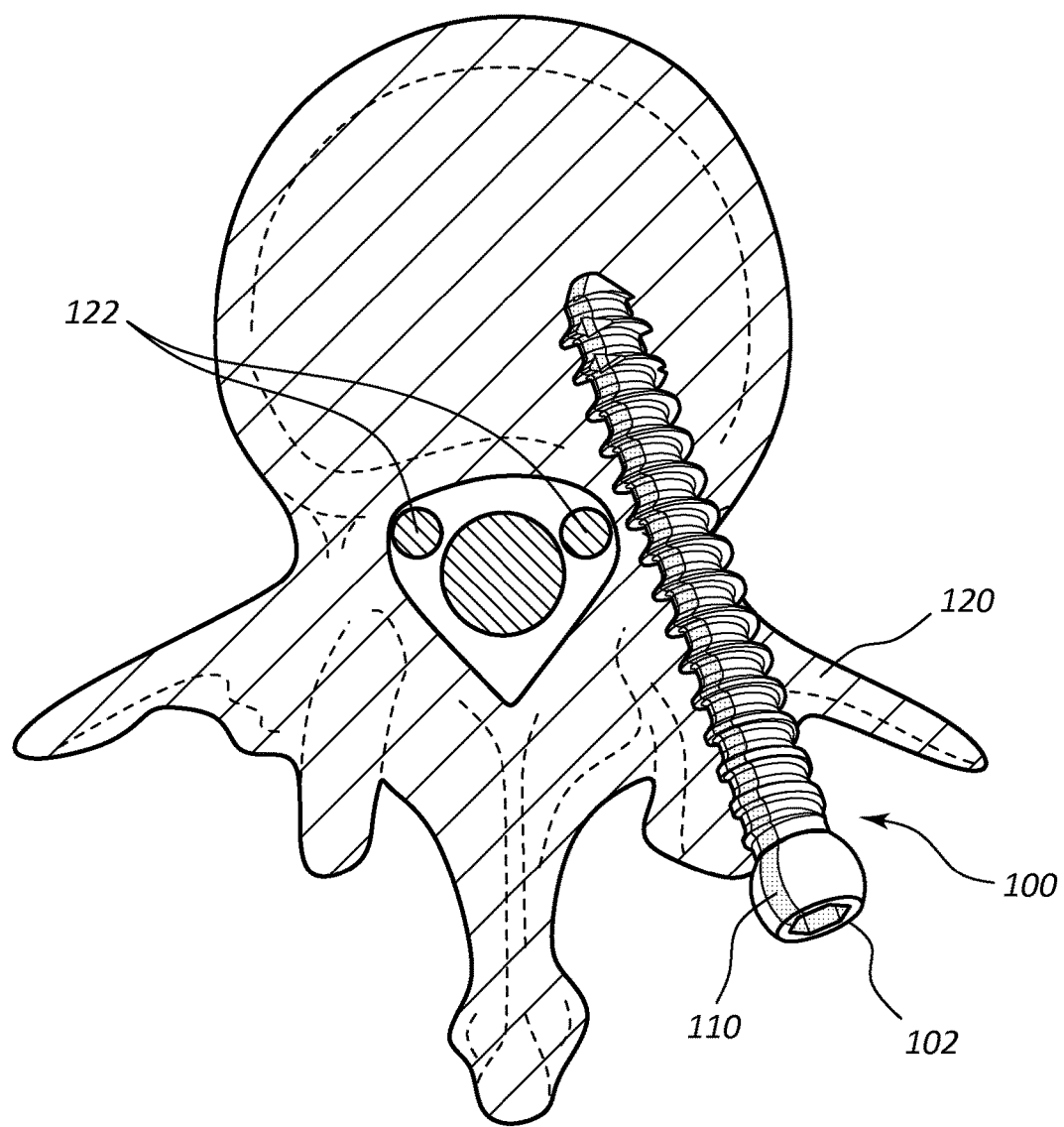
FIG. 3 shows placement of a pedicle screw such as that of FIG. 1 into a pedicle of a spine.
Figure 4:
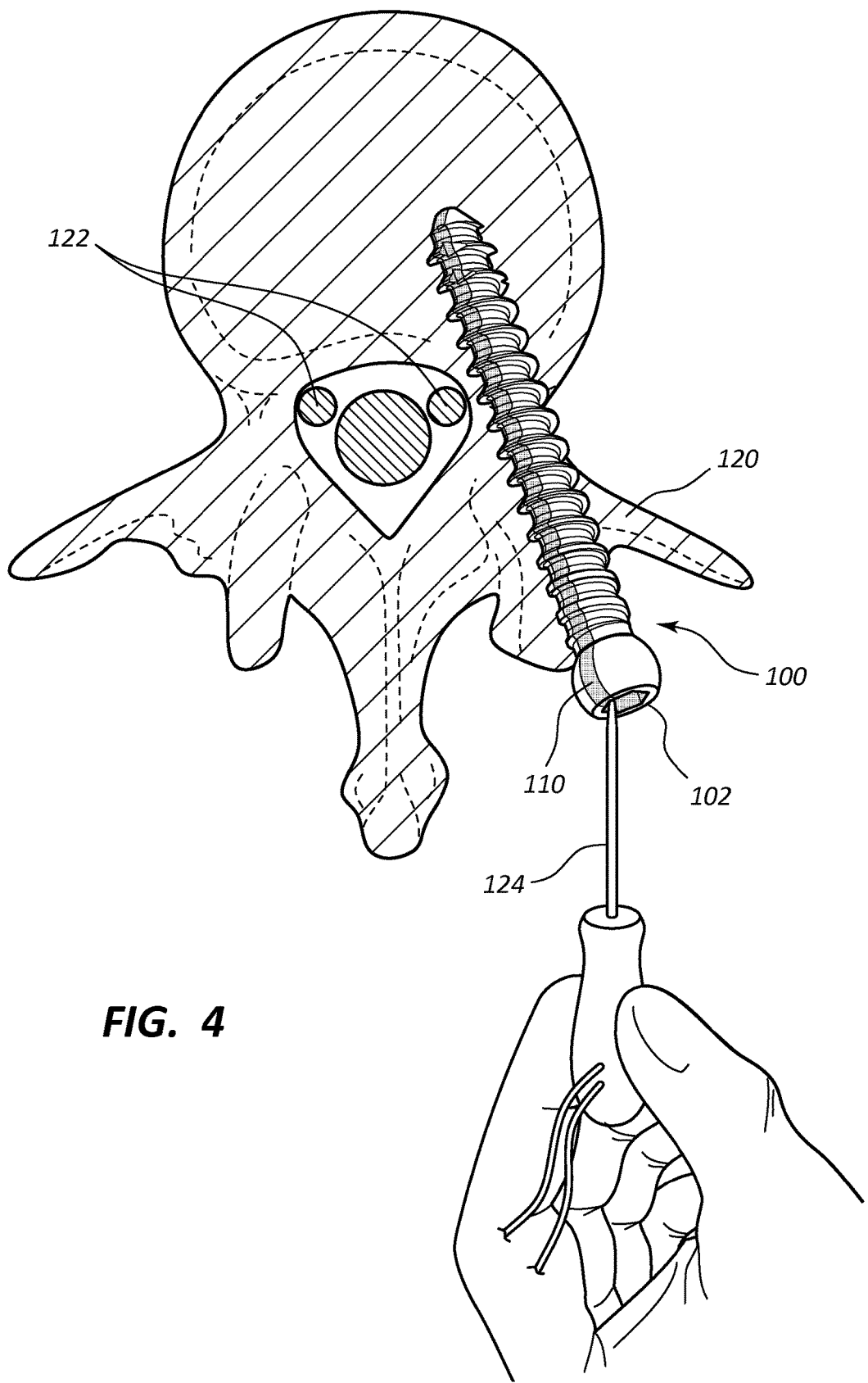
FIG. 4 shows how an electrical current may be applied to the pedicle screw including an electrically conductive portion, so that the current is preferentially delivered to the region of the screw (e.g., the side of the screw) that faces the nerve roots associated with the pedicle, aiding the surgeon in determining whether such screw placement is appropriate.

FIG. 3 shows how a screw 100 may be inserted through the pedicle bone 120, with electrically conductive portion 110 oriented towards the nerve root 122, so as to provide a sort of electrical "highway" along which electrical current may be directed from head 102 or other point of contact with an electrical probe towards the end of portion 110, which may terminate at the approximate location of nerve root 122. FIG. 4 shows a surgeon applying electrical current by contacting an electrical probe 124 to the proximal end of portion 110, e.g., within the interior of head 102. This allows the surgeon to determine (e.g., measure, obtain a reading, etc.) the electrical current or other characteristics associated with that particular proposed placement of the pedicle screw 100. For example, where the measured current or other electrical characteristic is too high, or otherwise exceeds a desired threshold (or drops below, depending on the particular characteristic), the surgeon may decide to reposition the pedicle screw (or tap). As shown, the inside (e.g., the entire interior surface) of head 102 may also be coated or otherwise provided with electrically conductive portion 110, to facilitate easier electrical contact between probe 124 and portion 110.

Figure 5A:
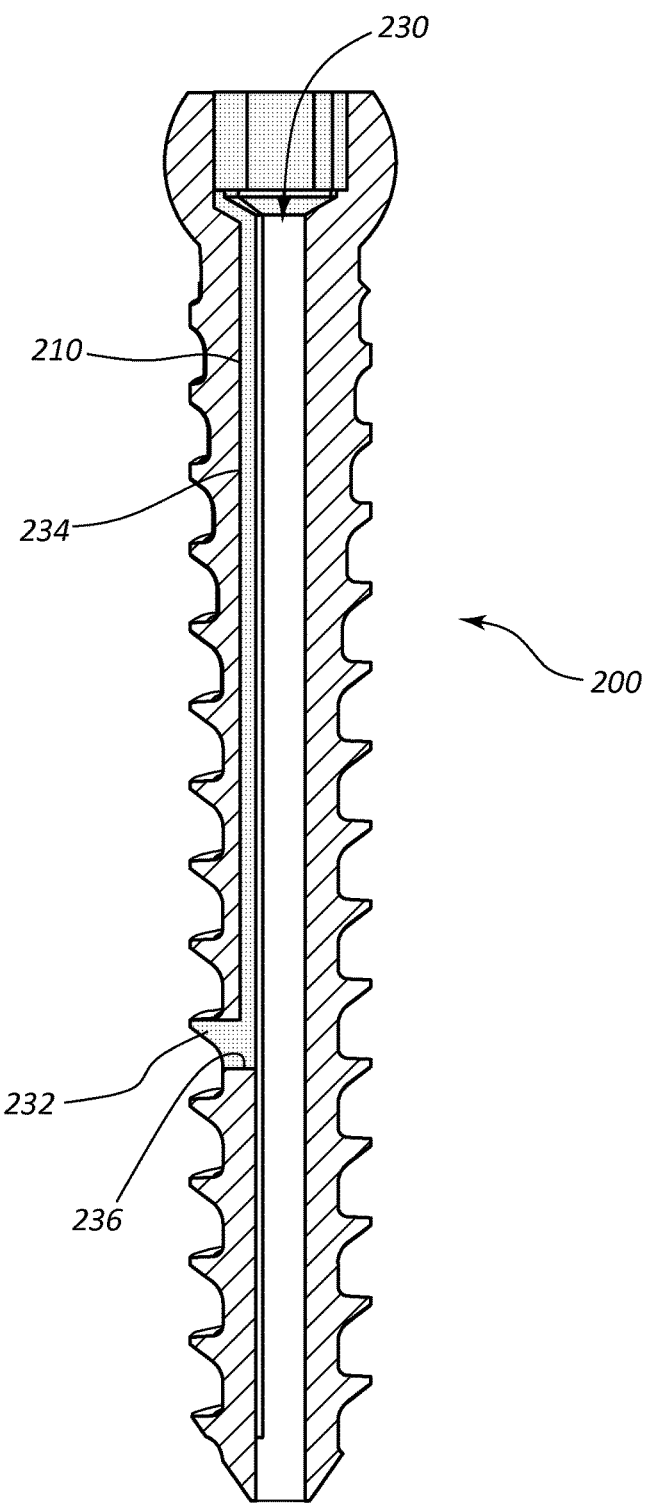
FIG. 5A illustrates another exemplary pedicle screw.

FIG. 5A illustrates another possible configuration of a pedicle screw 200, similar to screw 100. Screw 200 includes an internal cannula 230. Rather than running the electrically conductive portion down an exterior outside of the screw, a proximal upper portion of electrically conductive portion 234 is shown as being disposed within cannula 230. An exterior patch 232 is provided on the outside of screw 200, on a side and at a location (e.g., an axial location, between the distal and proximal ends) corresponding to the nerve root when the screw 200 is placed, so that upon placement of the screw 200 into the pedicle, the patch 232 would be facing, opposite, the nerve root 122 (see FIGS. 3-4), similar to the positioning of the end of portion 110 of screw 100. For example, the nerve root portion of the shaft, (where patch 232 would be disposed) may be about 1 to 2 cm from the distal tip of the device. Patch 232 and upper portion 234 may be electrically connected to one another by a passageway 236 through the sidewall of the screw 200. The entire portion 210 may thus include upper portion 234 (inside cannula 230), a portion of electrically conductive portion that passes through hole or passageway 236, and patch 232 (on the exterior of screw 200).

Placement of the majority of the electrically conductive portion within the interior of the pedicle screw (or a tap) may decrease unwanted dispersion of the electrical current as it passes from the point of probe contact to the desired location, on the nerve root portion of the shaft, opposite the nerve root.

Figure 5B:
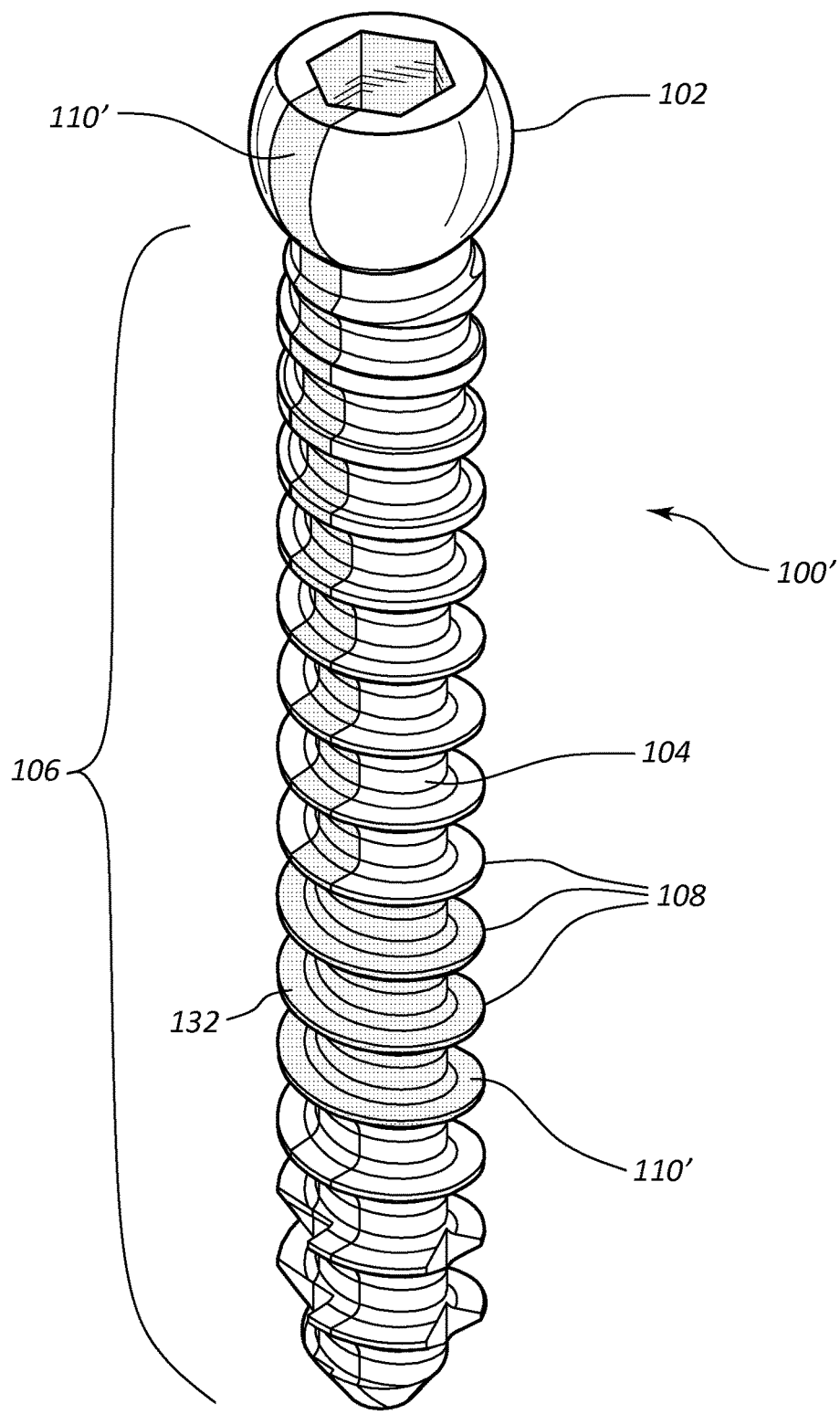
FIG. 5B illustrates yet another exemplary pedicle screw.
Figure 5C:
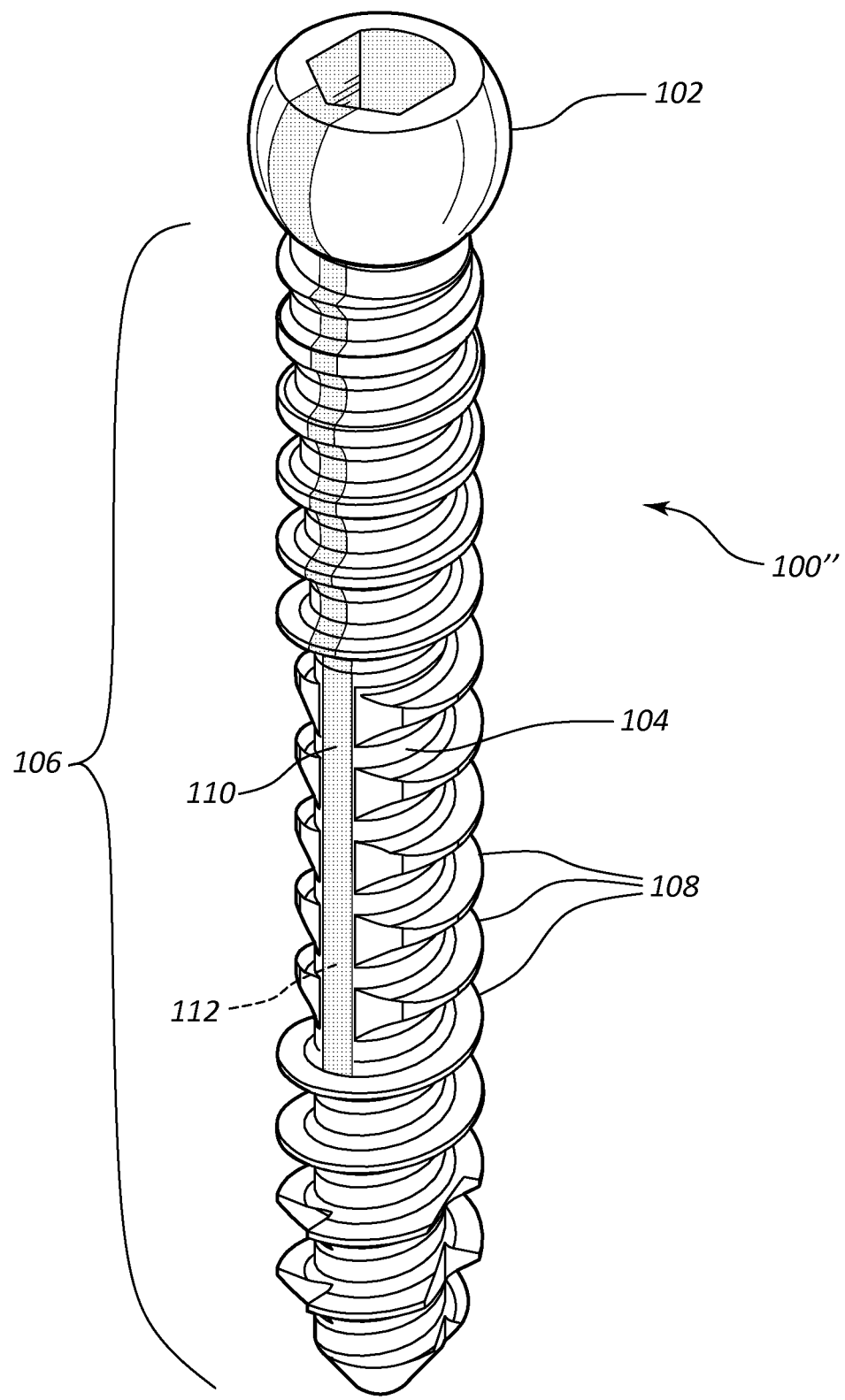
FIG. 5C illustrates yet another exemplary pedicle screw.

FIG. 5B illustrates another possible configuration, similar to screw 100 of FIG. 1, but in which screw 100' includes a portion of electrically conductive portion 110' that may extend radially around the entire perimeter (e.g., circumference of screw 100' at a location corresponding to the nerve root location of the screw. Such a screw is not directional in that it is not required to orient the screw 100' in a particular orientation to cause the nerve root location of the shaft to be facing towards nerve root 122, as portion 110' extends around the full perimeter at the desired location of the screw. Less than full radial extension around the perimeter of screw 100' (or a similarly configured tap) may also be possible. For example, extension could be any desired arc length (e.g., a sweep of 30°, 45°, 60°, 90°, 180°, 270° or any range defined between any such points).

FIG. 5C illustrates another screw 100" similar to screw 100, but which includes an unthreaded portion over the nerve root portion of the screw, as described in the inventor's earlier U.S. Pat. Nos. 8,740,956 and 9,084,633. Electrically conductive portion 110 may be aligned with the unthreaded portion 112, so that portion 110 runs down (e.g., down the center, or at least to) the unthreaded portion 112, as the purpose of each portion 110 and unthreaded portion 112 is to position the both so as to be opposite and facing the nerve root 122. Portion 110 may terminate at unthreaded portion 112, as shown. Alternatively, it could continue through portion 112, closer, or even to the distal end of the screw. An enlarged pad (similar to the enlarged pad 132 in FIG. 5B), larger in width than narrow strip 110 could be provided on the unthreaded portion 112, if desired.

While described herein principally in the context of pedicle screws, it will be appreciated that another embodiment of the present invention may provide similar benefits by placing the electrically conductive portion into a tap that is used in preparing a pedicle for placement of the pedicle screw. Such a tap may be somewhat differently configured than a pedicle screw (e.g., it may typically include a significantly longer proximal end to facilitate rotation and use of the tap to prepare the pedicle. That said, the tap may typically include proximal end structure that could be termed a "head", and a shaft, including a threaded portion, just as a pedicle screw does.

Figure 6:
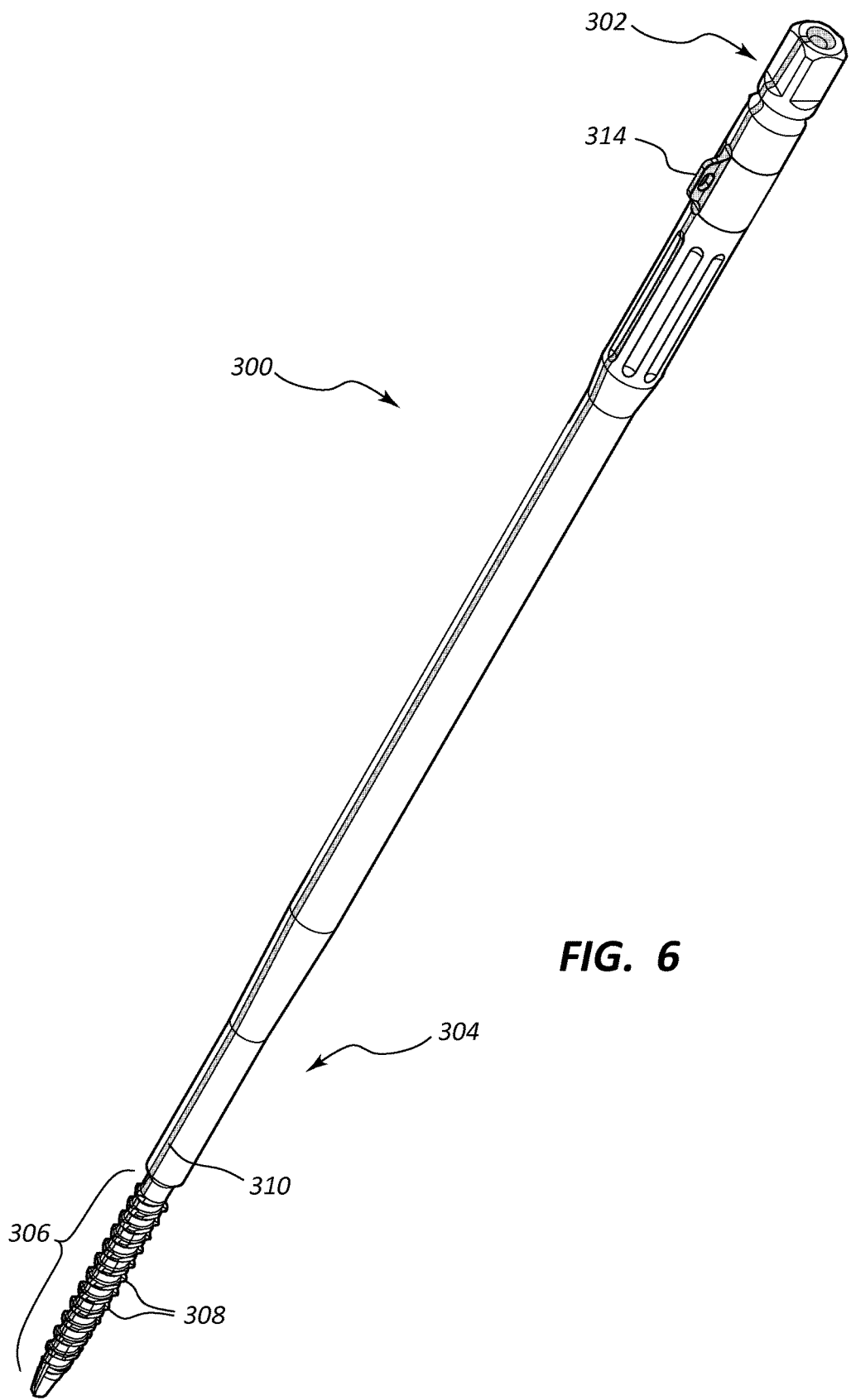
FIG. 6 illustrates an exemplary tap for insertion into a pedicle in preparation for placement of a pedicle screw, the tap including a head, shaft, and an electrically conductive portion.

FIG. 6 illustrates an exemplary tap 300 including a proximal head portion 302, a shaft 304 including a threaded portion 306 with threads 308. Just as described above relative to any of the pedicle screw embodiments, an electrically conductive portion 310 may be provided, having an electrical conductivity that is greater than the surrounding material (e.g., from which the remainder of shaft 304 and/or head 302 are formed of). Where the device including the electrically conductive portion is a tap, there may not be the same requirements as to biocompatibility of the materials of the tap tool as compared to a pedicle screw, as the tap is inserted into the pedicle for only a relatively short time, and then removed, while the pedicle screw may remain for a very long time. Any of the above described embodiments relative to placement of the electrically conductive portion, etc. may be equally applied to a tap including the technology.

Tap 300 of FIG. 6 is further shown as including a marker in the form of a flange 314, which is shown as being aligned with portion 310, to aid the surgeon in aligning tap 300 within the pedicle so that portion 310 is oriented towards, and facing the nerve root 122 during neuromonitoring. As shown, flange 314 may also advantageously facilitate easy attachment of an electrical clip for use during neuromonitoring.

Where the features are provided within a tap, the surgeon may insert the tap to prepare the pedicle for receipt of the pedicle screw, as he or she normally would, and when the tap is inserted in the location corresponding to that in which the pedicle screw would be placed, an electrical probe may be contacted with the electrically conductive portion 310 (e.g., by inserting the probe into head 302, where portion 310 extends into the interior of head 302). The portion 310 may provide an electrical "highway" from the point of probe contact to the nerve root portion of the shaft (i.e., that portion of shaft 304 which becomes positioned and oriented towards the nerve root 122), allowing the surgeon to obtain a measurement or reading of electrical current, or other electrical parameter. By comparing the reading to a given threshold value, the surgeon can determine whether the proposed pedicle screw placement is appropriate, or if repositioning is needed.

While described in the context of providing a "positive" electrically conductive coating or portion over the base material of the screw or tap, it will be appreciated that a similar result may be obtained by providing a "negative" non-conductive (or less conductive) coating or portion over all of the screw or tap (e.g., or at least that portion in the pedicle or patient body), except over a strip corresponding to the electrically conductive portion (e.g., portion 110 of FIG. 1). Such a reversal is also within the scope of the contemplated invention.

Numbers, percentages, or other values stated herein are intended to include that value, and also other values that are about or approximately the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing process, and may include values that are within 25%, within 20%, within 10%, within 5%, within 1%, etc. of a stated value. Furthermore, the terms "substantially", "similarly", "about" or "approximately" as used herein represents an amount or state close to the stated amount or state that still performs a desired function or achieves a desired result. For example, the term "substantially" "about" or "approximately" may refer to an amount that is within 25%, within 20%, within 10% of, within 5% of, or within 1% of, a stated amount or value.

Ranges between any values disclosed herein are contemplated and within the scope of the present disclosure (e.g., a range defined between any two values (including end points of a disclosed range) given as exemplary for any given parameter).

As used in this specification and the appended claims, the singular forms "a," "an" and "the" include plural referents unless the context clearly dictates otherwise.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A pedicle screw or a tap for insertion into a pedicle in preparation for placement of a pedicle screw, the pedicle screw or tap comprising:
   a head;
   a shaft attached to the head, the shaft comprising a threaded portion, the shaft and head of the comprising a material having a first electrical conductivity;
   an electrically conductive portion coated on or otherwise provided on the shaft, the electrically conductive portion of the shaft having a second electrical conductivity that is greater than the first electrical conductivity, wherein the electrically conductive portion extends longitudinally from the head to a distally disposed nerve root portion of the shaft, which nerve root portion of the shaft is located to be oriented towards a nerve root associated with a pedicle into which the pedicle screw or tap is placed during use;
   wherein the electrically conductive portion comprises an elongate strip of material that extends longitudinally down one side of an exterior of the shaft from the head to the nerve root portion of the shaft.

2. A pedicle screw or tap as in claim 1, wherein the pedicle screw or tap is a pedicle screw, the shaft comprising a biocompatible material.

3. A pedicle screw as in claim 2, wherein the biocompatible material from which the shaft is formed comprises titanium, and the electrically conductive portion comprises a material having an electrical conductivity greater than that of titanium.

4. A pedicle screw or tap as in claim 1, wherein the electrically conductive portion comprises a material selected from the group consisting of gold, silver, copper, and stainless steel.

5. A pedicle screw or tap as in claim 4, wherein the electrically conductive portion comprises gold.

6. A pedicle screw or tap as in claim 1, wherein the electrically conductive portion includes a proximal end that terminates within an interior of the head, so that a surgeon may insert an electrical probe into the head, contacting the proximal end of the electrically conductive portion.

7. A pedicle screw or tap as in claim 1, wherein the electrically conductive portion terminates short of a distal end of the shaft of the pedicle screw or tap, at a location so as to be opposite that of a nerve root when the pedicle screw or tap is inserted into the pedicle.

8. A pedicle screw or tap as in claim 1, wherein the pedicle screw or tap further comprises an internal cannula, an upper part of the electrically conductive portion being inside the internal cannula, and being electrically connected to an exterior patch of the electrically conductive portion on an outer surface of the pedicle screw or tap via a passageway through a sidewall of the pedicle screw or tap.

9. A pedicle screw or tap as in claim 8, wherein the exterior patch of the electrically conductive portion is disposed on the nerve root portion of the shaft.

10. A pedicle screw or tap as in claim 1, wherein the shaft comprises an unthreaded portion, wherein the electrically conductive portion is aligned with the unthreaded portion.

11. A pedicle screw or a tap for insertion into a pedicle in preparation for placement of a pedicle screw, the pedicle screw or tap comprising:

a head;

a shaft attached to the head, the shaft comprising a threaded portion, the shaft and head of the screw comprising a material having a first electrical conductivity;

an elongate electrically conductive portion coated or otherwise provided on one side of the shaft, the electrically conductive portion having a second electrical conductivity that is greater than the first electrical conductivity, wherein the electrically conductive portion extends longitudinally from the head of the pedicle screw or tap to a distally disposed nerve root portion of the shaft, which nerve root portion of the shaft is oriented towards a nerve root associated with a pedicle into which the pedicle screw or tap is placed during use;

wherein the shaft comprises graphite or titanium, and the elongate electrically conductive portion comprises a metal strip fitted into a groove of the shaft.

12. A pedicle screw or tap as in claim 11, wherein the electrically conductive portion comprises a material selected from the group consisting of gold, silver, and stainless steel.

13. A pedicle screw or tap as in claim 11, wherein the shaft comprises graphite.

14. A pedicle screw or tap as in claim 11, wherein the shaft comprises titanium.

15. A pedicle screw or tap as in claim 11, wherein the shaft comprises an unthreaded portion, wherein the electrically conductive portion is aligned with the unthreaded portion.

* * * * *